United States Patent
Betts et al.

(10) Patent No.: US 8,092,438 B2
(45) Date of Patent: Jan. 10, 2012

(54) DISPOSABLE ABSORBENT ARTICLE PRODUCTS WITH IMPROVED STAGES OF DEVELOPMENT IDENTIFICATION

(75) Inventors: Tysonn Yuievonn Betts, Colerain Township, OH (US); Ikdeep Singh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 149 days.

(21) Appl. No.: 12/498,430

(22) Filed: Jul. 7, 2009

(65) Prior Publication Data

US 2009/0266733 A1 Oct. 29, 2009

Related U.S. Application Data

(63) Continuation of application No. 11/509,362, filed on Aug. 24, 2006, now Pat. No. 7,582,075.

(51) Int. Cl.
*A61F 13/15* (2006.01)
*A61B 19/02* (2006.01)
*B65D 85/00* (2006.01)

(52) U.S. Cl. .............. 604/385.01; 604/385.02; 206/438; 206/440; 206/459.5

(58) Field of Classification Search ............. 604/385.01, 604/385.02; 206/37, 278, 524.1, 527, 529, 206/438, 440, 459.5
See application file for complete search history.

(56) References Cited

U.S. PATENT DOCUMENTS

| | | |
|---|---|---|
| 414,637 A | 11/1889 | Goodson |
| 416,794 A | 12/1889 | Mathieu |
| 421,901 A | 2/1890 | Breher |
| 421,902 A | 2/1890 | Britz |
| 437,686 A | 10/1890 | Geddes |
| 443,451 A | 12/1890 | Hunter |
| 443,508 A | 12/1890 | Emmet |
| 445,329 A | 1/1891 | Kerr |
| 451,279 A | 4/1891 | Sailor |
| 3,967,756 A | 7/1976 | Barish |
| 3,982,659 A | 9/1976 | Ross |
| 3,994,417 A | 11/1976 | Boedecker |
| 4,471,881 A | 9/1984 | Foster |
| 4,840,270 A | 6/1989 | Caputo et al. |
| 4,966,286 A | 10/1990 | Muckenfuhs |

(Continued)

FOREIGN PATENT DOCUMENTS

WO  WO-99/55213 A1  11/1999

(Continued)

OTHER PUBLICATIONS

Advertisements: "Introducing Pampers Phases", Sep. 1991.

(Continued)

*Primary Examiner* — Jacqueliene F Stephens
(74) *Attorney, Agent, or Firm* — Andrew A Paul; John P. Colbert

(57) ABSTRACT

A disposable absorbent article is provided. The article comprises one or more disposable absorbent articles having a configuration corresponding to a wearer's stage of development, the disposable absorbent articles being enclosed in a package; a brand indicator disposed on the package; a line-up indicator disposed on the package, the line-up indicator including visual indicia and narrative indicia; and a stage specific indicator disposed on the package. The line-up indicator and stage specific indicator associate the absorbent article configuration with a corresponding stage of development, the association enabling a consumer to identify the appropriate absorbent article configuration for a wearer. An array of disposable absorbent article configurations is also provided.

10 Claims, 4 Drawing Sheets

U.S. PATENT DOCUMENTS

| | | | |
|---|---|---|---|
| 4,971,220 | A | 11/1990 | Kaufman et al. |
| 5,050,737 | A | 9/1991 | Joslyn et al. |
| 5,065,868 | A | 11/1991 | Cornelissen et al. |
| 5,242,057 | A | 9/1993 | Cook et al. |
| 5,284,263 | A | 2/1994 | Papciak |
| 5,322,178 | A | 6/1994 | Foos |
| 5,366,104 | A | 11/1994 | Armstrong |
| 5,377,853 | A | 1/1995 | Papciak |
| 5,443,161 | A | 8/1995 | Jonese |
| 5,485,919 | A | 1/1996 | Samberg et al. |
| 5,591,155 | A | 1/1997 | Nishikawa et al. |
| 5,599,620 | A | 2/1997 | Huskey |
| 5,647,506 | A | 7/1997 | Julius |
| 5,715,841 | A | 2/1998 | Utecht |
| 5,732,716 | A | 3/1998 | Utecht |
| 5,785,179 | A | 7/1998 | Buczwinski et al. |
| 5,791,465 | A | 8/1998 | Niki et al. |
| 5,839,585 | A | 11/1998 | Miller |
| 5,885,264 | A | 3/1999 | Matsushita |
| 5,944,237 | A | 8/1999 | Gouldson |
| 6,024,094 | A | 2/2000 | Utecht |
| 6,092,690 | A | 7/2000 | Bitowft et al. |
| 6,168,022 | B1 | 1/2001 | Ward et al. |
| 6,229,061 | B1 | 5/2001 | Dragoo et al. |
| 6,269,969 | B1 | 8/2001 | Huang et al. |
| 6,269,970 | B1 | 8/2001 | Huang et al. |
| 6,296,144 | B1 | 10/2001 | Tanaka et al. |
| 6,315,114 | B1 | 11/2001 | Keck et al. |
| 6,401,968 | B1 | 6/2002 | Huang et al. |
| 6,412,634 | B1 | 7/2002 | Telesca et al. |
| 6,454,095 | B1 | 9/2002 | Brisebois et al. |
| 6,491,165 | B2 | 12/2002 | Kuske et al. |
| 6,568,530 | B2 | 5/2003 | Takahashi et al. |
| 6,601,705 | B2 | 8/2003 | Molina et al. |
| 6,648,864 | B2 | 11/2003 | Ronn et al. |
| 6,763,944 | B2 * | 7/2004 | Ronn et al. .................... 206/440 |
| 2002/0064323 | A1 | 5/2002 | Chin |
| 2002/0148742 | A1 | 10/2002 | Bisbal et al. |
| 2003/0136704 | A1 | 7/2003 | Burgess |
| 2004/0010240 | A1 | 1/2004 | Ronn et al. |
| 2008/0051749 | A1 | 2/2008 | Betts et al. |

FOREIGN PATENT DOCUMENTS

| | | |
|---|---|---|
| WO | WO-00/027268 A1 | 5/2000 |
| WO | WO-02/014172 A1 | 2/2002 |

OTHER PUBLICATIONS

"Introducing New! Luvs Phases", Jan. 1992.
"Introducing! The First Specially Designed Diaper Made Just for Your Walker", Sep. 1991.
"Dial-A-Wheel", Sep. 1991.

* cited by examiner

DISPOSABLE ABSORBENT ARTICLE PRODUCTS WITH IMPROVED STAGES OF DEVELOPMENT IDENTIFICATION

CROSS REFERENCE TO RELATED APPLICATION

This patent application is a continuation of U.S. application Ser. No. 11/509,362, filed Aug. 24, 2006 now U.S. Pat No. 7,582,075, the substance of which is incorporated herein by reference.

FIELD OF THE INVENTION

The present application relates generally to disposable absorbent articles. The present application also relates to a system for facilitating consumers' identification and selection of the appropriate absorbent article configuration for a particular wearer.

BACKGROUND OF THE INVENTION

Disposable absorbent articles such as diapers, training pants, adult incontinence products and feminine care products are designed to absorb and contain bodily waste to prevent soiling of the body and clothing. The disposable absorbent articles typically comprise a single design available in different sizes to fit a variety of wearers ranging from newborns to active toddlers. The design of the diaper typically affects performance, such as ability to absorb and contain bodily waste. The size of the diaper typically affects fit, for example, the size of the diaper waist opening, the size of the openings around the thighs, and the length or "pitch" of the diaper.

The problem with a one design fits all approach is that a single configuration may not be appropriate for every level of activity and capability. For instance, caregivers for newborns and immobile infants may desire a soft, yet bulky design which wraps the wearer and is gently on the wearer's skin whereas once the infant becomes actively mobile it may be more desirable to have a contoured trim fit design providing the wearer more freedom of movement. Other designs may also be desired as the toddler grows and becomes more and more capable of independent activity. For instance, a pull on diaper design may be beneficial for toddlers participating in the dressing experience. Similarly, a training diaper design may be appealing to a toddler in the toilet training stage which makes a wearer aware when a discharge of bodily waste has occurred while at the same time providing the necessary protection to the wearer's clothing. It is difficult to design a single product configuration exhibiting each of these attributes. Thus, there is a need for a variety of disposable diaper designs matching a particular wearer's capability and/or level of activity.

Although providing a variety of diaper designs matching an infant or toddler's capability and/or level of activity may meet a consumer need, physical sizes of infants and toddlers vary throughout their development. As a result, different product designs are preferably made available in the same sizes. For instance, a disposable diaper designed for a crawling toddler may be available in the same size as a configuration designed for a walking toddler and/or a configuration designed for a toddler participating in the dressing experience. Merchandising systems typically display and arrange disposable diapers according to size numbers.

This proliferation of disposable diaper offerings does have its drawbacks, however. In particular, store displays may include an abundance of disposable diaper products. For example, many manufacturers offer several versions of disposable diaper products in different "tiers" or "levels". These could represent different sub-needs or different levels of technology with different corresponding price points. As a result, it can be confusing for consumers to select the proper product in terms of appropriate size/stage/features and an appropriate tier level and to navigate among the offerings for a desired product even if such basic information such as desired brand and size is known. In addition, consumers shopping for disposable diaper products often have babies or small children with them, resulting in less ability to intently focus upon the multiplicity of product offerings. As such, a consumer, given the overwhelming range of options, may select the wrong product (i.e., a product other than that intended) or a product which may not be optimum (i.e., wrong stage, wrong features, wrong size). Either could lead to a less than ideal use experience.

Thus, there remains a need for disposable absorbent articles and arrays of disposable absorbent articles, that make it easier for a caregiver to select a design from a variety of configurations that matches a particular wearer's needs.

SUMMARY OF THE INVENTION

In one embodiment, an article includes (a) one or more disposable absorbent articles having a configuration corresponding to a wearer's stage of development, the absorbent articles being enclosed in a package; (b) a brand indicator disposed on the package; (c) a line-up indicator disposed on the package, the line-up indicator including visual indicia and narrative indicia; and (d) a stage specific indicator disposed on the package. The line-up indicator and stage specific indicator associate the absorbent article configuration with a corresponding stage of development, the association enabling a consumer to identify the appropriate absorbent article configuration for a wearer.

In another embodiment, a package includes (a) a front panel having a top and bottom portion; (b) one or more disposable absorbent articles having a configuration corresponding to a wearer's stage of development; (c) a stage communication system disposed on the top portion for associating the absorbent article configuration with a corresponding stage of development, the association enabling a consumer to identify the appropriate absorbent article configuration for a wearer; and (d) an informational corridor disposed on the bottom portion. The informational corridor includes a size indicator, a weight range indicator and at least one product benefit indicator.

In yet another embodiment, an array of disposable absorbent article products include (a) an absorbent article of a first configuration corresponding to a wearer's first stage of development, the absorbent article of the first configuration being enclosed in a first package; (b) an absorbent article of a second configuration corresponding to a wearer's second stage of development, the absorbent article of the second configuration being enclosed in a second package; and (c) a stage communication system disposed on each of the first and second packages. The stage communication system comprises a brand indicator; a line-up indicator, the line-up indicator including visual indicia and narrative indicia; and a stage specific indicator. In addition, the line-up indicator and stage specific indicator associate the first and second absorbent article configurations with respective first and second stages of development, the association enabling a consumer to identify the appropriate absorbent article configuration for a wearer.

The foregoing articles, packages and systems can be employed relative to disposable diapers and other absorbent articles having a range of sizes and a variety of designs or configurations.

BRIEF DESCRIPTION OF THE DRAWINGS

While the specification concludes with claims which particularly point out and distinctly claim the invention, it is believed the various embodiments will be better understood from the following description taken in conjunction with the accompanying drawings, in which:

DETAILED DESCRIPTION OF THE INVENTION

As used herein, the term "absorbent article" refers to devices which are designed to absorb and contain bodily exudates, and, more specifically, refers to devices which are placed within, against, or in proximity to, the body of the wearer to absorb and contain the various exudates discharged from the body.

As used herein, the term "caregiver" refers to a person other than the child, such as, a parent, babysitter, family member, teacher, day care worker, or other person who is able to provide sufficient assistance or supervision to a child using an absorbent article.

As used herein, the term "chassis" refers to the main structure of a diaper, with other features added to form the composite diaper structure.

As used herein, the term "stage(s) of development" refers to a level of emotional and cognitive maturity and/or the physical abilities of an individual including locomotion, mobility, motor skills and coordination.

As used herein, the term "diaper" refers to an absorbent article generally used by infants and incontinent persons that is worn about the lower torso of the wearer.

As used herein, the term "disposable" describes absorbent articles which are generally not intended to be laundered or otherwise restored or reused as an absorbent article (in other words, they are generally intended to be discarded after a single use, and, preferably, to be disposed of in an environmentally compatible manner).

References to identifying a "size" is used herein to include a direct or indirect identification of a disposable diaper or other absorbent article size, such as by number or letter (for example, "Size 3" or "Size A"), by direct description (for example, "Small" or "Large"), or by any combination thereof, and whether expressed or discernible visually, audibly or otherwise.

As used herein, "visual indicia" is an identifying marking which may include any illustration, painting, photograph, drawing, picture, logo, hologram or graphic that visually communicates or signals characteristics of a product in use.

As used herein, "narrative indicia" is an identifying marking which may include letters, numbers or a combination thereof that communicates or signals characteristics of a product in use.

Figure 1:
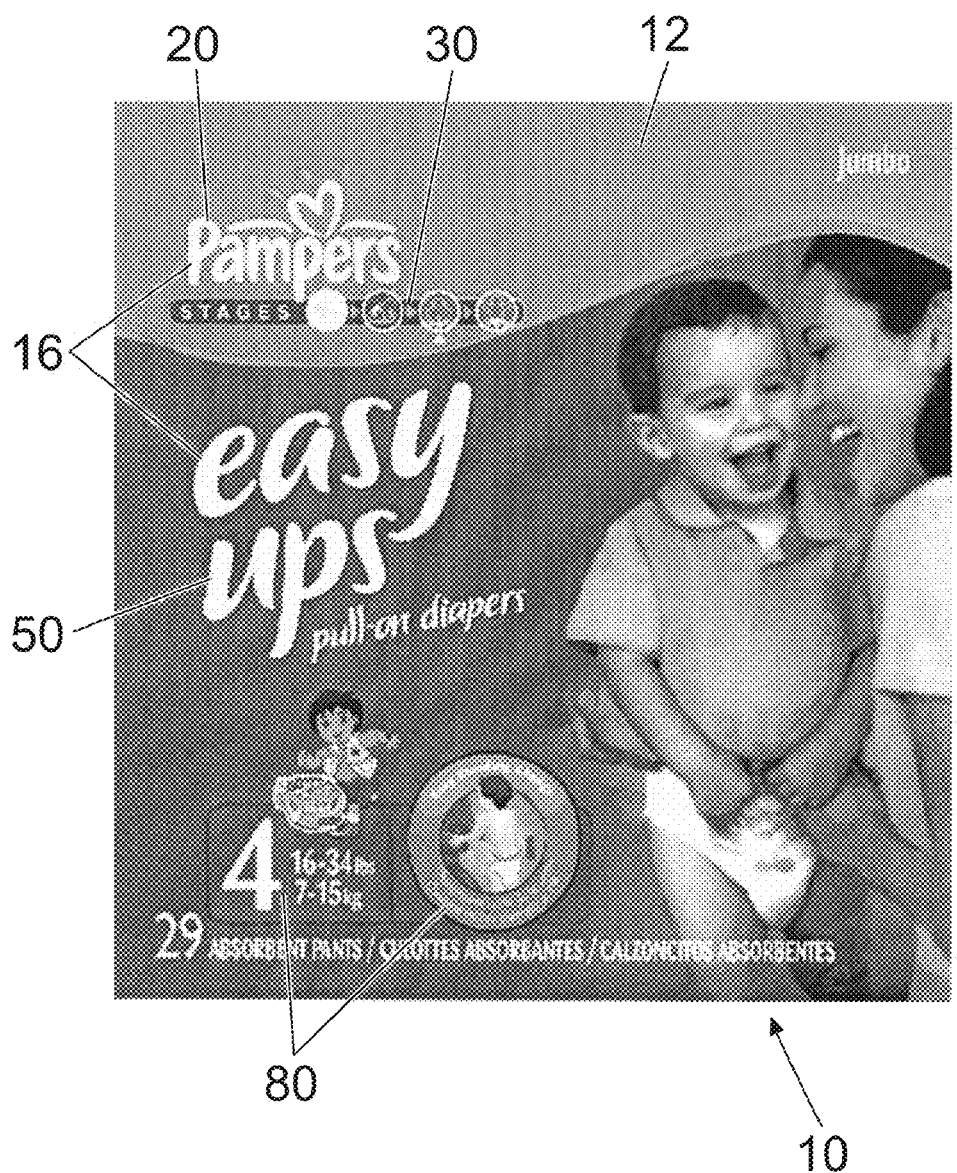
FIG. 1 illustrates an exemplary front panel of a package of disposable absorbent articles in accordance with one embodiment.
Figure 2:
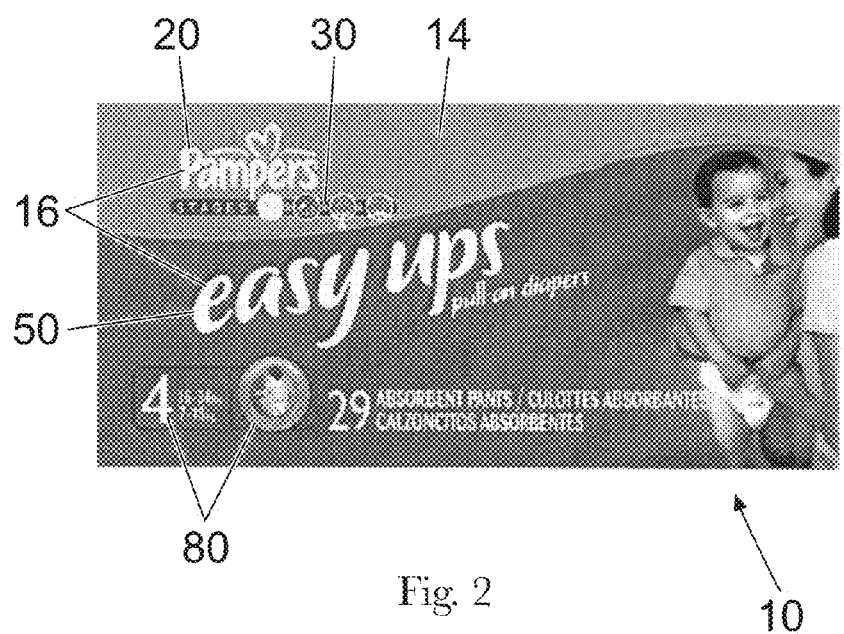
FIG. 2 illustrates an exemplary end panel of a package of disposable absorbent articles in accordance with one embodiment.

Referring to FIG. 1, package 10 includes a front panel 12 having a top and bottom portion and has one or more disposable absorbent articles (not shown) enclosed therein, and a stage communication system 16. In one embodiment, the stage communication system 16 includes a brand indicator 20, a line-up indicator 30 and a stage specific indicator 50, each of these indicators disposed on the front panel 12. In another embodiment, the stage communication system 16 is disposed on the top portion of the front panel 12. As described in more detail below, the stage communication system 16 communicates both brand benefits and the progressive nature of a line-up of absorbent article configurations more clearly to consumers. Referring to FIG. 2, the package 10 includes an end panel 14.

The disposable absorbent articles can be packaged in a variety of containers such as bags, boxes or cartons. In one embodiment, as shown in FIG. 1, the absorbent articles are packaged in a poly bag. In another embodiment, the package 10 may be a plastic "shrink-wrap" container.

The package and array of absorbent articles described herein may be applicable to a number of absorbent article products, such as diapers, training pants, adult incontinence products and feminine hygiene garments. For example, feminine hygiene garments may be made available in a variety of designs depending on a wearer's level of activity. However, the embodiments illustrated in FIGS. 1 and 2, include an assortment of disposable diapers made available in a variety product configurations where each configuration includes distinguishable characteristics comprising structural differences addressing a wearer's stage of development. The stages of development may range from newborns to active toddlers seeking independence.

For example, a first stage of development might cover a pre-locomotive phase and include newborns in a bonding stage with mom and other immobile infants whose level of activity might include a little more than head raising or rolling over. A second stage of development might cover an exploring stage comprising a crawling phase and include curious toddlers developing activity in the form of sitting up and holding objects and mobility in the form of scooting, rolling, crawling and assisted walking. A third stage of development might cover a learning stage and include toddlers capable of doing things by themselves such as dressing and developing coordination which enables them to stand, walk and run without losing balance. A fourth stage of development might cover a training stage and include toddlers undergoing toilet training, attempting to achieve independence, such as climbing, and overall undergoing a transition from baby to child. Other stages are contemplated.

For each or any of the aforementioned stages of development, a separate absorbent article configuration may be provided. For example, for the first stage of development, the absorbent article configuration may comprise a chassis designed to swaddle the wearer like a blanket and include a blanket like feel. This configuration might also include special structural features like an umbilical cord notch and also ornamental features such as graphics which include pastel colors and back to sleep logos. For the second stage of development, a second absorbent article configuration may comprise a chassis designed to gently conform to the wearer in order to enable more freedom of movement. For this second configuration, the chassis might be contoured having a relatively narrow crotch region, a stretchable high back region and a low cut front region and also include bright color graphics. This configuration may also include features like flexible fasteners and high stretch sides to facilitate easy, struggle-free changes of a toddler in a standing or lying position. For the third stage of development, the third absorbent article configuration may comprise a pull on chassis designed to look more like underwear that a wearer can put on and take off enabling him or her to participate in the dressing experience. For the fourth stage of development, the fourth absorbent article configuration may comprise a chassis providing the comfort of underpants and the protection of a diaper while at the same time include a wetness indicator that enables the wearer to recognize the discomfort associated with wetting.

Since infants and toddlers experience stages of development at different rates, multiple sizes may be provided for each absorbent article configuration. As a result, different absorbent article configurations are made available in overlapping size ranges. For example, the first absorbent article configuration might be available in a size one, a size two and a size three, while the second absorbent article configuration might be available in a size three, a size four and a size five. The third absorbent article configuration might be available in a size three, a size four and a size five while the fourth absorbent article might be available in a size four, a size five and a size six, and so on.

Overlapping size ranges make it difficult for a consumer to choose the right product configuration matching a particular wearer's stage of development. For this reason, an article is provided that facilitates consumers' selection of an absorbent article from a variety of configurations.

Still referring to FIGS. 1 and 2, the brand indicator 20 includes a term corresponding to a brand of absorbent article products. As used herein, the term "brand" refers to any term, symbol, design or combination thereof that identifies and differentiates a seller's product or service. The term "brand" also encompasses the set of expectations associated with a product or service which typically arise in the minds of consumers. In one example, brand indicator 20 includes the term PAMPERS. In another example, brand indicator 20 may include the term LUVS. Each of these brand indicators are trademarks of absorbent article products manufactured by The Procter and Gamble Company.

Figure 3:
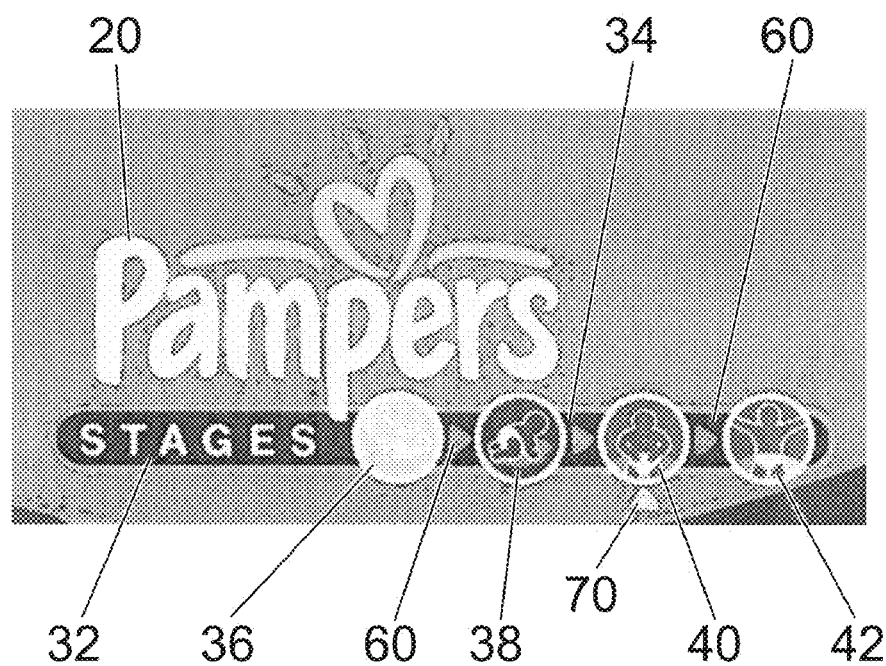
FIG. 3 illustrates the brand indicator and the line-up indicator shown in FIGS. 1 and 2.

The line-up indicator 30 assists consumers in identifying the appropriate absorbent article configuration for a particular wearer by associating each absorbent article configuration with a corresponding stage of development. As shown in FIG. 3, the line-up indicator 30 includes narrative indicia 32 and visual indicia 34 in order to convey the various stages of development to the consumer. In one embodiment, the narrative indicia 32 is located in a proximal relationship with the visual indicia 34. In one example, the narrative indicia 32 and the visual indicia 34 are arranged horizontally. In another example, the narrative indicia 32 and the visual indicia 34 might be arranged vertically. Exemplary narrative indicia, may include, without limitation, the terms "stages," "etapas," "etapes," "changes with me," "collection," "transitions," "changes," "steps," "next steps," "baby steps," and "progress."

As further shown in FIG. 3, the visual indicia 34 may include a sequence of icons or pictorial representations corresponding to a wearer's stages of development. In one embodiment, the visual indicia 34 includes four icons or indicia, each visibly different and each corresponding to a different stage of development. For example, a first indicia 36 corresponding to the first stage of development might display a newborn engaged in an action or activity, such as head raising or rolling over. A second indicia 38 corresponding to the second stage of development might display a baby engaged in an action or activity, such as crawling, scooting, rolling, sitting up, holding objects or assisted walking. A third indicia 40 corresponding to the third stage of development might display a toddler engaged in an action or activity, such as standing, walking, running or dressing. A fourth indicia 42 corresponding to the fourth stage of development might display a toddler engaged in an action or activity, such as celebrating, toilet training or climbing. As shown in FIG. 3, any of the depictions can show a baby as engaged in an action or activity corresponding to a particular stage of development. By matching the stage of development of a wearer with the stage of development exhibited by the visual indicia 34, the consumer can choose the right product configuration for their particular wearer. While round or circular visual indicia 34 are shown in FIG. 3, visual indicia of other shapes may also be used, if desired.

In another embodiment, the line-up indicator 30 may be provided on a display panel disposed above the store shelves on which the absorbent article configurations are displayed for sale. In another embodiment, the line-up indicator 30 may be disseminated in electronic or print media. Electronic media includes internet, television, terrestrial and satellite radio or any media broadcast through electronic means. Printed media includes all forms of visual or sensory media not transmitted via electronic means, for example, magazines, billboards, store displays, flyers, inserts and newspapers. In another embodiment, the line-up indicator 30 may be disseminated in kiosks and 3-D displays. Kiosks and 3-D displays can be interactive and can incorporate media to provide multiple avenues for disseminating visual and narrative indicia to the consumer simultaneously.

In the embodiment shown in FIG. 3, the sequence of icons or indicia are located adjacent to one another in a horizontal arrangement. That is, the first indicia 36 is located adjacent to the second indicia 38, which is located adjacent to the third indicia 40, which is located adjacent to the fourth indicia 42. In another embodiment, the sequence of icons or indicia may be disposed in a vertical arrangement.

Still referring to FIG. 3, the line-up indicator 30 may also include a transitional indicator 60 disposed between the first indicia 36 and the second indicia 38. The transitional indicator 60 signals to the consumer a transition or progression from one stage of development to the next stage of development, for example, from the first stage of development to the second stage of development. Additional transitional indicators 60 may be disposed between the second indicia 38 and the third indicia 40 and between the third indicia 40 and the fourth indicia 42. While transitional indicator 60 is shown in FIG. 3 as an arrow, indicators of other symbols or shapes may also be used, if desired. The transitional indicator 60 further emphasizes the progressive nature of the various absorbent article configurations.

In another embodiment, the line-up indicator 30 also includes a stage identifier 70 located in a substantially normal direction to the visual indicia 34. The stage identifier 70 signals to the consumer the particular type of absorbent article configuration enclosed in the package 10. For example, as shown in FIG. 3, the stage identifier 70 indicates that a third absorbent article configuration corresponding to a third stage of development is enclosed in the package 10. While stage identifier 70 is shown in FIG. 3 as an arrow, identifiers of other symbols or shapes may also be used, if desired.

The line-up indicator may also include a common color scheme that is associated with a particular stage of development. The term "color," as used herein, relates to the phenomenon of visual perception that enables one to differentiate otherwise identical objects. In one embodiment, a background color scheme is chosen for the visual indicia 34 that matches a color scheme of various absorbent article configurations. In one example, the first indicia 36 has a first background color, for example, yellow, the second indicia 38 has a second background color, for example, purple, the third indicia 40 has a third background color, for example, red, and the fourth indicia 42 has a fourth background color, for example, blue or pink. As a result, the color scheme of the first indicia 40 matches the color scheme of a first absorbent article configuration, while the second, third, and fourth indicia match the color scheme of second, third and fourth absorbent article configurations, respectively. In another embodiment, the indicia may have two or more background colors to signal that a particular absorbent article configuration is available in different versions, for example, blue for boys and pink for girls. The use of a visual indicia color scheme that matches a color scheme of various absorbent article configurations is used to facilitate consumers' identification and selection of the appropriate absorbent article configuration for a particular wearer.

Similar to the line-up indicator 30, the stage specific indicator 50 assists consumers in identifying the appropriate absorbent article configuration for a particular wearer by associating each absorbent article configuration with a corresponding stage of development. As shown in FIGS. 1 and 2, the stage specific indicator 50 includes a product name associating a product configuration with the particular stage of development for which the product is designed. For example, the first absorbent article configuration could be named SWADDLERS, while the second, third, and fourth product configurations could be named CRUISERS, EASY UPS and FEEL 'N LEARN, respectively. In another embodiment, the second product configuration could be named ACTIVE FIT. Each of the product names listed are trademarks of absorbent article products manufactured by The Procter and Gamble Company. In yet another embodiment, a different stage specific indicator 50 may be located below its corresponding indicia. For example, located below the first indicia 36 could be the name SWADDLERS, while located below the second, third and fourth indicia could be the names CRUISERS, EASY UPS and FEEL 'N LEARN, respectively.

Figure 4:
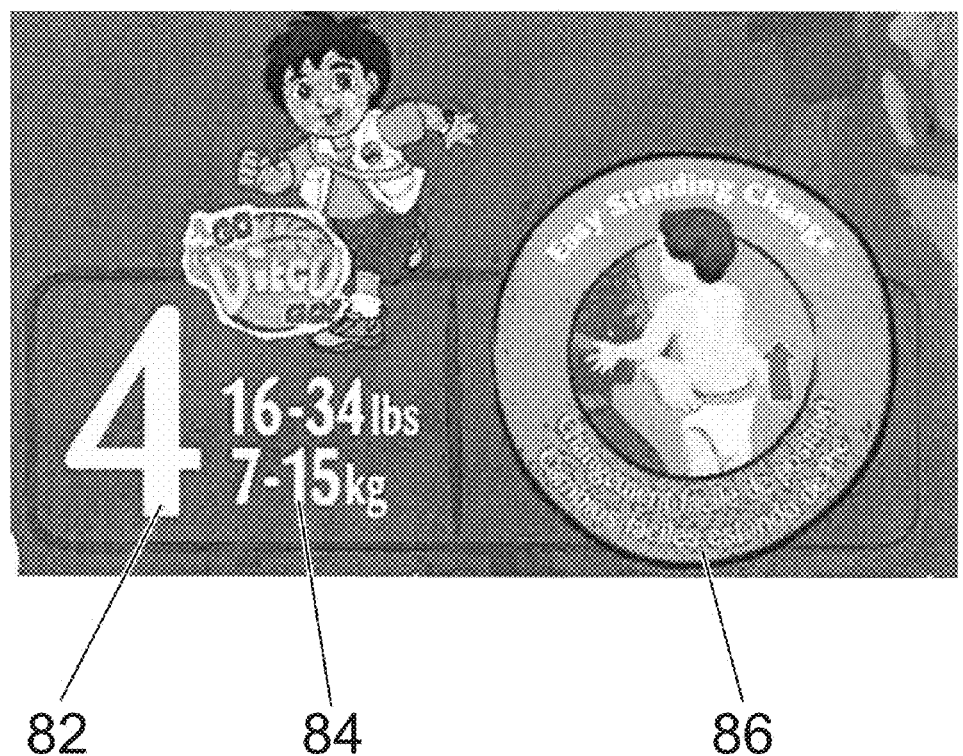
FIG. 4 illustrates the informational corridor shown in FIGS. 1 and 2.

The package 10 may also include an informational corridor 80 disposed on the package 10. In one embodiment, as shown in FIG. 4, the informational corridor 80 includes a size indicator 82, a weight range indicator 84, and at least one product benefit indicator 86, each these indicators disposed on the front panel 12. In another embodiment, the informational corridor 80 is disposed on the bottom portion of front panel 12. In yet another embodiment, two or more product benefit indicators may be provided.

The informational corridor 80 further assists consumers in choosing the right product configuration matching a particular wearer's stage of development. In particular, the size indicator 82 and corresponding weight range indicator 84 facilitate consumers' selection of an absorbent article from a variety of configurations. In the embodiment shown in FIG. 4, the size indicator is "4" and the corresponding weight range indicator is "16-34 lbs (7-15 kg)." Exemplary size indicators and corresponding weight range indicators may include, without limitation, the following:

| Size Indicator/Stage of Development | Weight Range Indicator |
|---|---|
| N/first | Up to 10 lbs (up to 4.5 kg) |
| 1/first | 8-14 lbs (4-6 kg) |
| 2/first | 12-18 lbs (5-8 kg) |
| 3/second | 16-28 lbs (7-13 kg) |
| 4/second | 22-37 lbs (10-17 kg) |
| 4/third | 16-34 lbs (7-15 kg) |
| 5/second | 27+ lbs (12+ kg) |
| 5/third | 30-40 lbs (14-18 kg) |
| 6/second | 35+ lbs (16+ kg) |
| 6/third | 37+ lbs (17+ kg) |
| 3T-4T/fourth | 26-40 lbs (12-18 kg) |
| 4T-5T/fourth | 34-50 lbs (16-23 kg) |

Other size indicators and weight range indicators are contemplated.

In the embodiment shown in FIG. 4, the at least one product benefit indicator 86 includes information-bearing indicia to convey the benefit associated with a particular absorbent article configuration. The information-bearing indicia may include visual or narrative features or combinations thereof. Exemplary product benefit indicators, may include, without limitation, visual and/or narrative indicia which communicate a product benefit such as, an absorb away liner, blanket like feel, umbilical notch, contoured shape, high stretch sides, flexible fasteners, a 3-way fit, easy standing change, a pull on chassis designed to look like underwear, and a feel wet liner that enables a wearer to recognize the discomfort associated with wetting. In one embodiment, as shown in FIG. 4, the information-bearing indicia includes the term "Easy Standing Change" together with an image of a toddler standing on his own while the caregiver changes the diaper.

In the embodiment shown in FIG. 4, the series of informational corridor indicators are located adjacent to one another in a horizontal arrangement. That is, the size indicator 82 is located adjacent to the weight range indicator 84, which is located adjacent to the at least one product benefit indicator 86. In another embodiment, the series of informational corridor indicators may be disposed in a vertical arrangement.

In another embodiment, the variety of absorbent article configurations may be displayed on store shelves in an arrangement that facilitates the consumer's selection. For example, the absorbent article configurations may be arranged in a first sequential order according to the stages of development and in a second sequential order according to size.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article comprising:
   a) one or more disposable absorbent articles having a configuration corresponding to a baby's stage of development, the disposable absorbent articles being enclosed in a package;
   b) a brand indicator disposed on the package; and
   c) an informational corridor disposed on the package, wherein the informational corridor includes a size indicator, a weight range indicator and at least one product benefit indicator, the product benefit indicator including visual indicia and narrative indicia;
   wherein the size indicator is located adjacent to the weight range indicator and the weight range indicator is located adjacent to the at least one product benefit indicator; and
   wherein the product benefit indicator conveys the benefit associated with the absorbent article configuration, the association enabling a consumer to identify the appropriate absorbent article configuration for a baby.

2. The article of claim 1, wherein the brand indicator comprises a term corresponding to a brand of disposable absorbent article products.

3. The article of claim 1, wherein the product benefit indicator indicia is selected from the group consisting of absorb away liner, blanket like feel, umbilical notch, contoured shape, high stretch sides, flexible fasteners, a 3-way fit, easy standing change, a pull on chassis and a feel wet liner.

4. The article of claim 1, wherein the baby's stage of development is selected from the group consisting of a first stage of development, a second stage of development, a third stage of development and a fourth stage of development.

5. The article of claim 4, wherein the first stage of development comprises a bonding stage.

6. The article of claim 4, wherein the second stage of development comprises an exploring stage.

7. The article of claim 4, wherein the third stage of development comprises a learning stage.

8. The article of claim 4, wherein the fourth stage of development comprises a training stage.

9. The article of claim 1, further comprising a stage specific indicator disposed on the package.

10. The article of claim 1, wherein the package includes indicia illustrating an absorbent article on a wearer.

* * * * *